(12) United States Patent
Bühler et al.

(10) Patent No.: US 8,857,485 B2
(45) Date of Patent: Oct. 14, 2014

(54) APPARATUS FOR WELDING TOGETHER THERMOPLASTIC HOSES

(75) Inventors: Peter Bühler, Schwarzenberg (CH); Willy Fluder, Stansstad (CH)

(73) Assignee: Reed Electronics AG, Schachen (CH)

( * ) Notice: Subject to any disclaimer, the term of this patent is extended or adjusted under 35 U.S.C. 154(b) by 345 days.

(21) Appl. No.: 13/264,572

(22) PCT Filed: Apr. 12, 2010

(86) PCT No.: PCT/CH2010/000100
§ 371 (c)(1),
(2), (4) Date: Nov. 7, 2011

(87) PCT Pub. No.: WO2010/118546
PCT Pub. Date: Oct. 21, 2010

(65) Prior Publication Data
US 2012/0138235 A1 Jun. 7, 2012

(30) Foreign Application Priority Data
Apr. 14, 2009 (CH) .................................. 589/09

(51) Int. Cl.
| | |
|---|---|
| B26D 5/00 | (2006.01) |
| B29C 65/00 | (2006.01) |
| B29C 65/02 | (2006.01) |
| B29C 65/04 | (2006.01) |
| B32B 37/28 | (2006.01) |
| B29C 65/20 | (2006.01) |
| A61M 39/14 | (2006.01) |
| B29C 65/78 | (2006.01) |
| B29L 23/00 | (2006.01) |

(52) U.S. Cl.
CPC ......... *B29C 65/7841* (2013.01); *B29C 65/2084* (2013.01); *B29C 66/857* (2013.01); *B29C 66/1142* (2013.01); *B29L 2023/007* (2013.01); *B29C 65/2046* (2013.01); *B29C 66/5221* (2013.01); *B29C 66/65* (2013.01); *B29C 66/80* (2013.01); *A61M 39/146* (2013.01)
USPC ..................... 156/353; 156/304.1; 156/304.2; 156/359; 156/502; 156/503; 156/510

(58) Field of Classification Search
USPC ........... 156/304.1, 304.2, 353, 359, 502, 503, 156/510
See application file for complete search history.

(56) References Cited

U.S. PATENT DOCUMENTS

| | | | | |
|---|---|---|---|---|
| 5,802,689 | A | * | 9/1998 | Sano ............................. 29/33 T |
| 6,026,882 | A | * | 2/2000 | Yamada et al. ............... 156/433 |
| 2002/0174956 | A1 | | 11/2002 | Sano et al. |

FOREIGN PATENT DOCUMENTS

| | | |
|---|---|---|
| EP | 0 507 321 | 10/1992 |
| EP | 0 778 123 | 6/1997 |
| EP | 0 953 431 | 11/1999 |
| WO | WO 2005/000565 | 1/2005 |

\* cited by examiner

*Primary Examiner* — Phillip Tucker
*Assistant Examiner* — Christopher C Caillouet
(74) *Attorney, Agent, or Firm* — D. Peter Hochberg; Sean F. Mellino; Richard A. Wolf (57) ABSTRACT

An apparatus for welding together thermoplastic hoses comprising two clamping units which in part can be rotated and displaced relative to each other. The two clamping units each have two clamping jaws which comprise through-passages between the clamping jaws in which the hoses can be inserted continuously parallel to each other and squeezed transversely to each other. The apparatus further comprises a heatable blade for severing the hoses and melting the cut edges thereof between the clamping units. An intermediate piece is disposed between the clamping jaws of the clamping units, thereby separating the clamped hoses from each other, and at least one of the two clamping units has inner and outer clamping jaws, wherein the inner clamping jaws are held by the outer clamping jaws and can be adjusted together. In a closed position, the inner clamping jaws and the intermediate piece can be rotated with each other.

16 Claims, 6 Drawing Sheets

APPARATUS FOR WELDING TOGETHER THERMOPLASTIC HOSES

This application is a National Stage application of International Application No. PCT/CH2010/000100, filed on Apr. 12, 2010, which claims priority of Swiss Application Serial No. 00589/09 filed on Apr. 14, 2009.

BACKGROUND OF THE INVENTION

1. Field of the Invention

The invention relates to a device for welding together thermoplastic hoses with two clamping units which can be rotated and displaced in parts relative to each other and have two clamping units having clamping jaws and with through-passages between the clamping jaws in which the hoses can be inserted continuously parallel to each other and squeezed transversely to each other, and with a heatable blade for cutting through the hoses and melting their cut edges between the clamping units.

Such devices are used for example in biotechnology and in medicine, when it is necessary to produce sterile hose connections between a cell culture and a nutrient medium or between a dialysis patient and a bag for the rinse solution. By squeezing the hose, fluid contained in it is prevented from coming out during the welding process and possibly contaminating the surroundings. At the end of the welding process, all the hose ends are closed. This is also called total containment under moist welding conditions.

2. Description of the Prior Art

A prior-art apparatus is known from EP 0 778 123 in which after the hoses are cut through, one of the clamping units is turned by 180° and then the hose sections that come into alignment with each other through this turning are welded to each other. In the through-passages of the two clamping units, the hoses in this apparatus are stacked directly on top of each other and are squeezed therein directly transversely on each other. It is not apparent how a hose which after turning and being welded on both sides is joined with a container, can again come out of the clamping units. Owing to the configuration of the turning support, the known apparatus is quite voluminous.

In the apparatus from EP 0 507 321, provision is also made for two clamping units that can be turned relative to each other. Into them, the hoses are inserted in two through-passages placed at a distance from each other, and then squeezed perpendicular to their common positional plane. The means for supporting the clamping units is not described.

SUMMARY OF THE INVENTION

It is the task of the invention in particular to provide an apparatus of the type named initially which permits exact welding together of two liquid-filled hoses with no leakage of liquid out into the surroundings and which is designed to be compact.

The problem is solved by an apparatus for welding together of thermoplastic hoses as per claim 1, which is characterized in that between the clamping jaws of the clamping unit, separating clamped hoses from each other, an intermediate piece is placed, and at least one of the two clamping units comprises inner as well as outer clamping jaws, wherein the inner clamping jaws are held by the outer clamping jaws, are adjustable jointly with them, and can be turned in a closed setting as well as together with the intermediate piece enclosed by them in the outer clamping jaws.

Due to squeezing, the diameter of the hoses diminishes in the squeezing direction and at the same time becomes larger transverse to the squeezing direction. By having the hoses in the invention-specific apparatus as with EP 0 778 123 be squeezed transversely to each other, their cross sections as squeezed together and to be welded with each other occupy less space than in EP 0 507 321, in which the squeezed-together cross sections are placed longitudinal to each other. This makes possible a more compact design of the apparatus than in EP 0 507 321.

Due to the intermediate pieces provided according to the invention, the hoses in their squeezed-together state, are kept separate from each other in separate through-passages, otherwise than in EP 0 507 321, which permits a better and more exact determination of their cross sections to be welded to each other, and also ensures that adjoining hoses will not be welded in undesired fashion.

Also making a considerable contribution to compact design is the division according to the invention of the clamping jaws of a clamping unit into inner and outer clamping jaws, wherein only the inner clamping jaws need to be configured to be turnable in the outer clamping jaws. By this means it is not necessary to rotate the entire clamping unit.

The hoses do not need to be fully squeezed together over the entire length of the through passages, which typically can amount to between 30 mm and 70 mm. It suffices if this is the case only in relatively short squeezing zones extended in the longitudinal direction only 1 mm and 10 millimeters, for example, whereby these squeezing zones needing to adjoin the opposing sides of the two clamping devices with very small mutual intervals. The remaining length of the through-passages, in which these have a wider cross section vis-à-vis the squeezing zones, serves only for supplemental support and guidance of the hoses and in what follows is designated as the holding zone.

In the squeezing zones, the through-passages preferably are provided with a rectangular cross section with the longer sides of the rectangle being directed parallel to each other, wherein the inner sides of the rectangle are defined by planar contact surfaces at webs of the intermediate pieces and the outer rectangular sides by planar contact surfaces at web-like walls of the clamping jaws or of the inner clamping jaws. The width of the rectangular cross sections should be just double the wall thickness of the hoses to be welded to each other. To better expel the liquid from the areas of the squeezing zone, the width of the rectangular cross section can correspond to 50% to 70% of the double wall thickness of the hoses to be welded to each other.

In contrast, the length of the rectangular sides may be larger than necessary for the hoses to be welded to each other, and especially can be dimensioned to be sufficiently long for the thicker of the hoses to be joined to each other, if the hoses are held at the level of the turning axis of the inner clamping jaws, as by the profile of the intermediate pieces still to be described. Owing to the rectangular cross sections of the through-passages, the hose cross section in the cut plane between the clamping units is determined very precisely and additionally is rotationally symmetrical, which ensures exact fitting together of the hose cross sections after turning.

The already mentioned webs of the intermediate pieces can additionally have projections above and below as a hose limitation on both contact surfaces, resulting in a dual T-shaped web profile. By this means, the rectangular through-passage is limited in its length in the area of the squeezing zone, wherein the hose cross section of the squeezed hoses can be determined with still greater precision in the cut plane between the clamping units. This ensures that the hose cross sections will fit together even more exactly after turning. The length of the rectangular through-passage in the area of the squeezing zone preferably amounts to 120-140% of the diameter of the hoses to be squeezed.

In the area of the holding zones, as already mentioned, the through-passages have a cross section larger than the cross section in the squeezing zones, whereby this cross section preferably widens in a direction away from the intermediate pieces. Due to the outward widening, the rectangular cross sections come to lie advantageously close together in the squeezing zones, which has a favorable effect on the compact design of the inner clamping jaws.

Additionally, due to the outward widening, in the area of the holding zones, the intermediate pieces can be provided with a dual C-shaped profile, in which the hoses can be continuously pre-secured when inserted into the through-passages. Preferably this profile is adapted to the diameter of the hoses to be welded. Additionally, as already mentioned, the profile holds the hoses at the level of the turning axis of the inner clamping jaws, due to which the length of the rectangular sides of the through-passages can be dimensioned to be larger in the squeezing zone than is necessary for the hoses to be welded to each other. If in addition the clamping jaws or the inner clamping jaws in the area of the holding zones have a flat contact zone vis-à-vis the hoses, all that is needed is to change the intermediate pieces to adjust the apparatus to hoses with a different diameter.

By changing only the intermediate pieces, the invention-specific apparatus can also be adapted to hoses with differing wall thickness, wherein merely the thickness of intermediate pieces or their already-mentioned webs that determine the mutual interval needs to be suitably selected. With this, the projections of the webs can also be appropriately dimensioned to adapt the rectangular through-passages in the area of the squeezing zone to the various hose diameters.

The inner clamping jaws are preferably secured against turning in the outer clamping jaws outside the closed setting, which facilitates insertion and removal of hoses as well as at least one motorized closure of the clamping units also.

To further enhance the user-friendliness of the invention-specific apparatus, the intermediate pieces can be kept on a holding structure. So that the intermediate piece is turnable between the inner clamping jaws together with them, this intermediate piece must be released from its holder in the closing setting.

Additionally, a simple design of the invention-specific apparatus results if one of the clamping jaws or of the outer clamping jaws of the claming unit is mounted in stationary fashion, and, for insertion or removal of the hoses from the through-passages, only the other clamping jaw and the intermediate pieces are movably mounted with their holding devices. With this, preferably a motor moves them along a linear guide device.

Preferably the clamping unit with the inner and outer clamping jaws, including the intermediate piece placed in it, is configured to be rotationally symmetric relative to half turns of the inner clamping jaws and of the intermediate piece in the outer clamping jaws. By this means, after a welding process and removal of the hoses welded to each other, the invention-specific apparatus is again usable for another welding pass, without the inner clamping jaws and the intermediate piece placed between them needing first to be again turned in the outer clamping jaws back into their initial setting.

For hoses filled with liquids, to ensure that after squeezing of the hoses, there is no more residual liquid in the hose sections between the two clamping units, which could come out into the surroundings when the hoses are separated, and/ or could evaporate on the hot blade, the interval of the two clamping units or of the above-mentioned squeezing zones must not be too large. A suitable interval when the hoses are cut through is 3-6 mm, for example, preferably 5 mm. So that no liquid-filled hose pockets can form between the two clamping units, the hoses should additionally not be squeezed on the two clamping units simultaneously, but rather one after the other. For welding together of the hoses, the named interval can if necessary additionally be reduced by several millimeters, for example.

BRIEF DESCRIPTION OF THE DRAWINGS

In what follows, the invention will be explained in greater detail using embodiment examples in connection with the drawings. Shown are.

DETAILED DESCRIPTION OF THE PREFERRED EMBODIMENTS

Figure 1:
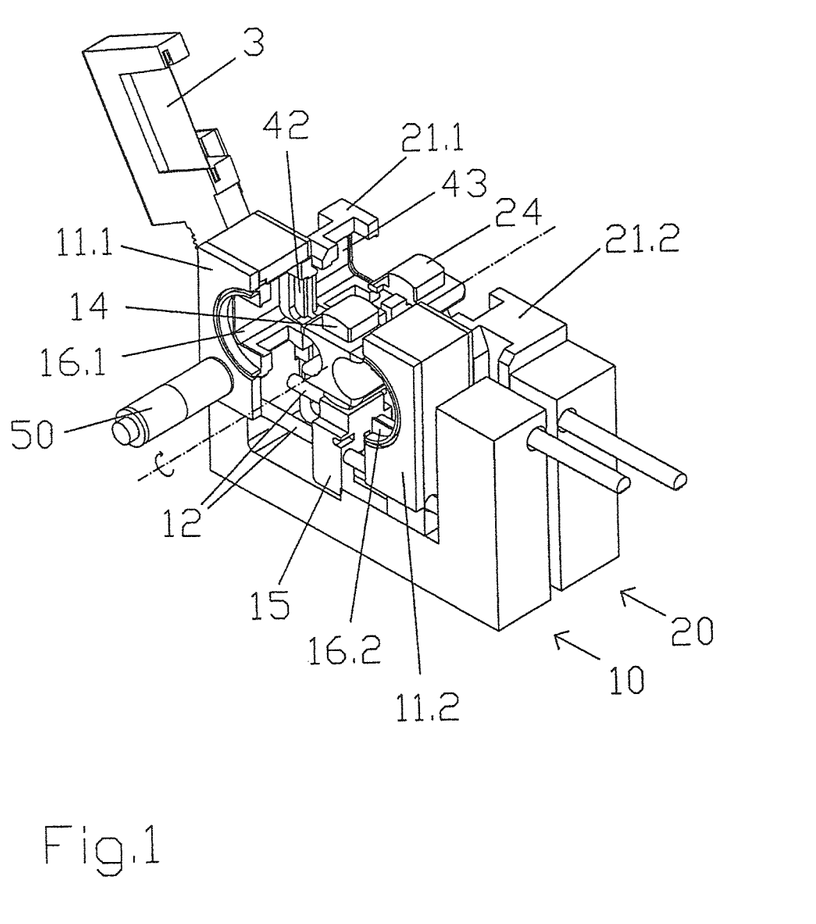
FIG. 1 is an invention-specific apparatus with two clamping units in a perspective view of its front side.
Figure 2:
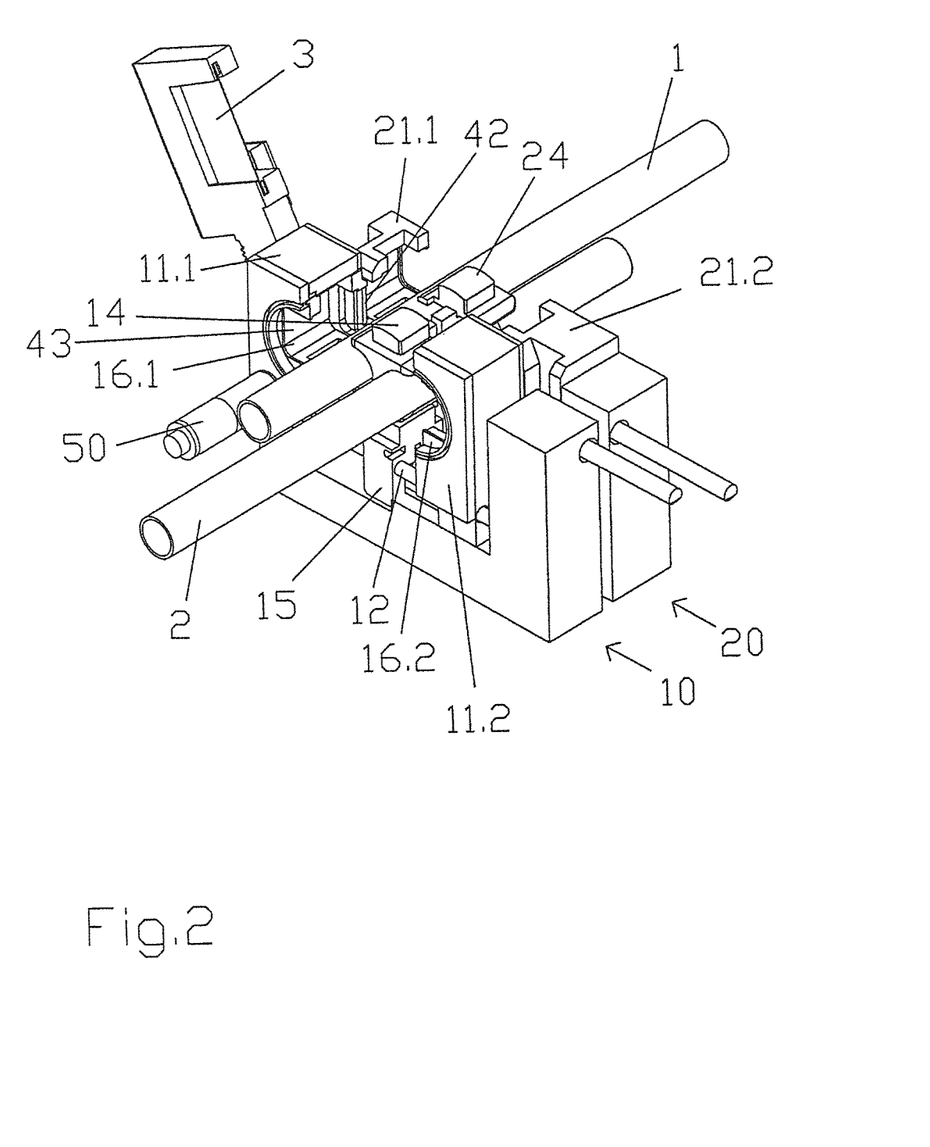
FIG. 2 is the apparatus from FIG. 1 with inserted hoses.
Figure 3:
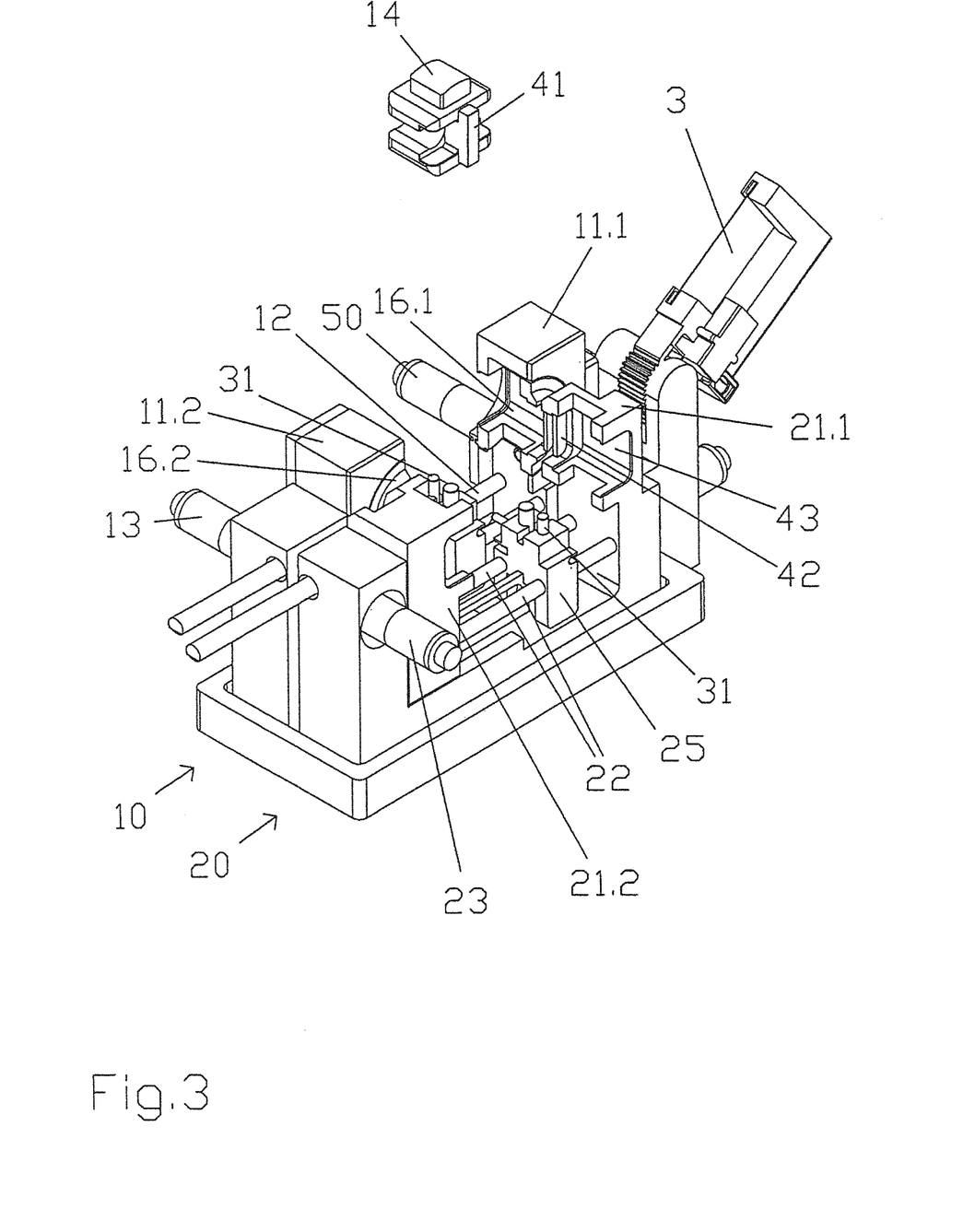
FIG. 3 is the apparatus from FIG. 1 in a perspective rear view.

FIGS. 1-3 show an invention-specific apparatus for welding together of thermoplastic hoses, where, for the sake of distinguishing individual parts, not all parts of the apparatus are depicted in all the figures. In FIGS. 1 and 3, the apparatus is depicted without hoses and in FIG. 2 with two continuous hoses 1 and 2 running parallel to each other.

Figure 6A:
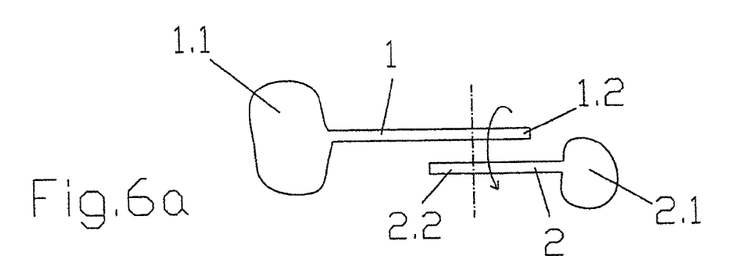
FIG. 6a schematically shows two containers with hoses closed at ends in front.

Only short sections are shown of hoses 1 and 2. In actuality, as depicted in FIG. 6a, the opposite ends of hoses 1, 2 could be closed with containers 1.1 and 2.1 and the two others closed with 1.2 and 2.2. Additionally, the hoses could be filled with liquid.

The invention-specific apparatus comprises two clamping units 10 and 20 placed in close proximity to each other, between which a heatable blade 3 can be pivoted for cutting through and for welding hoses 1 and 2 with each other.

Both clamping units 10 and 20 comprise two clamping jaws, which are designated by 11.1 and 11.2 in clamping unit 10 and by 21.1 and 21.2 in clamping unit 20.

Clamping jaws 11.1 and 11.2 are movable along horizontal linear guides 12 and 22 relative to clamping jaws 11.1 and 21.1 that are permanently locationally fixed at one end of these guides, and can be adjusted thereby from their open setting depicted in FIGS. 1 and 2 into the closed setting according to FIG. 4b, 4c or 5b, 5c. For this adjustment, two motors 13 and 23 depicted in FIG. 3 are provided, which act via toothed rods on clamping jaws 11.2 and 21.2.

For both clamping units 10 and 20, between the clamping jaws an intermediate piece 14 and 24 is placed, with these intermediate pieces, as evident in FIG. 2, separating hoses 1 and 2 from each other. Intermediate pieces 14 and 24 are held on holders 15 and 25, which, like clamping jaws 11.2 and 21.2, are able to be shifted in linear fashion on guides 11 and 22.

Figure 4A:
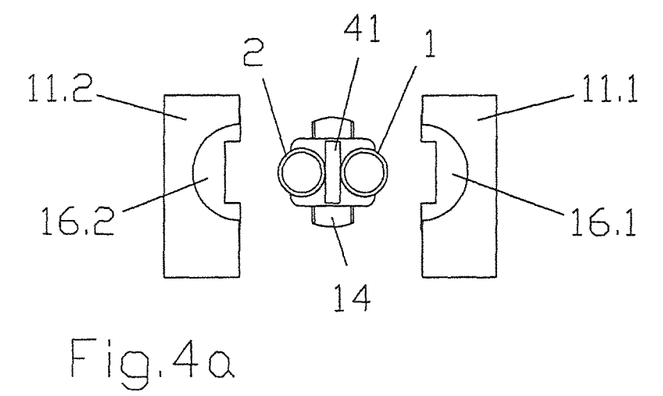
FIG. 4a is a view of the rear of only the clamping jaws and of the intermediate piece with inserted hoses of the front-side clamping unit in an open state.

Into the clamping jaws 11.1 and 11.2 of clamping unit 10, designated hereinafter as the outer clamping jaws, inner clamping jaws 16.1 and 16.2 are inserted. FIGS. 4a and 4a show views of this clamping unit in an opened state. In the closed setting of clamping unit 10 as per FIG. 4b or 5b, inner clamping jaws 16.1 and 16.2, together with the intermediate piece 14 enclosed by them, form a turnable capsule in outer clamping jaws 11.1 and 11.2. FIGS. 4c and 5c show clamping device 10 with this capsule, turned relative to its depiction in FIGS. 4b and 5b.

In the open setting of clamping unit 10, the two inner clamping jaws 16.1 and 16.2 are secured against torsional motion in the outer clamping jaws 11.1 and 11.2, with this for example achievable using pins, which engage from outer clamping jaws 11.1 and 11.2 into inner clamping jaws 16.1 and 16.2, and which pins, governed for example via a connecting link guide, are retracted when they reach the closed setting from inner clamping jaws 16.1 and 16.2 The connection of the intermediate piece 14 to its holder 15 can be configured in appropriate fashion through pins 31 and be canceled upon reaching the closed setting.

As relates to their contour relative to hoses 1 and 2, inner clamping jaws 16.1 and 16.2 of clamping unit 10 and clamping jaws 21.1 and 21.2 of clamping unit 20 are configured identical to each other. Additionally, inner clamping jaws 16.1 and 16.2 of clamping unit 10 are rotationally symmetrical relative to half turns. The same holds true for intermediate pieces 14 and 24, with intermediate piece 14 connectable to holder 15 in two turning settings displaced by 180° to each other.

The inner clamping jaws 16.1 and 16.2 together with intermediate piece 14 in the closed setting of clamping unit 10 define two through-passages, separated from each other by intermediate piece 14 for hoses 1 and 2. The same holds true for clamping unit 20, here with clamping jaws 21.1 and 21.2 together with intermediate piece 24 defining the through-passages. In the closed settings of both clamping units 10 and 20, their through-passages align with each other, so that hoses 1 and 2 can be fixed continuously in them.

In the longitudinal direction of the hoses, the through-passages have two zones with differing cross sections, namely on one side a squeezing zone and on the other a holding zone. In the squeezing zones, this cross section is rectangular and on its longer sides is bordered by webs 41 on the intermediate pieces and by web-like walls 42 on the clamping jaws. The width of the rectangular cross section along their shorter sides exactly matches the dual wall thickness of hoses 1, 2. The thickness of the web-like walls 42 and thus the longitudinal extension of the squeezing zones typically is only about 1-6 mm. On both clamping units 10 and 20, the squeezing zones border on their opposite sizes adjoining with the smallest mutual interval.

In the holding zones, the cross section of the through-passages relative to the rectangular cross section in the squeezing zones expands outward, away from intermediate pieces 14, 24, with the intermediate pieces there having a dual C-shaped profile adapted to the diameter of the hoses. The contact surfaces 43 that lie opposite intermediate pieces 14, 24 on the clamping jaws are, in contrast, configured to be flat.

Figure 4B:
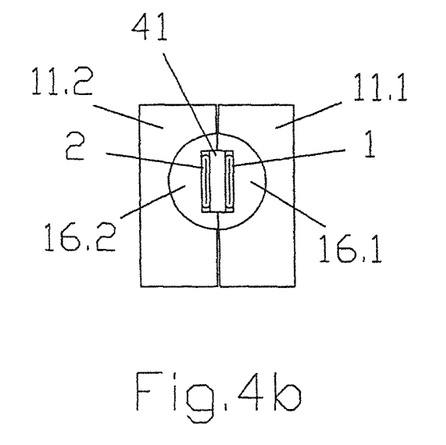
FIG. 4b is the clamping unit from FIG. 4a in its closed state.
Figure 4C:
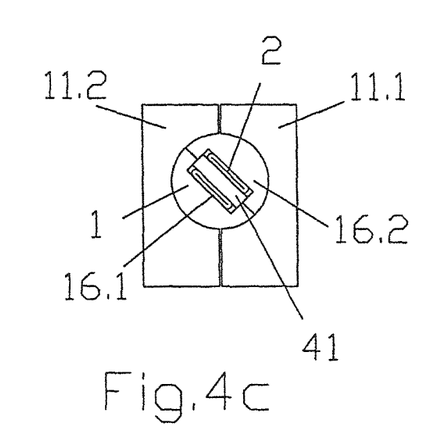
FIG. 4c is the clamping unit from FIG. 4b with turned inner clamping jaws, intermediate piece and hoses.
Figure 5A:
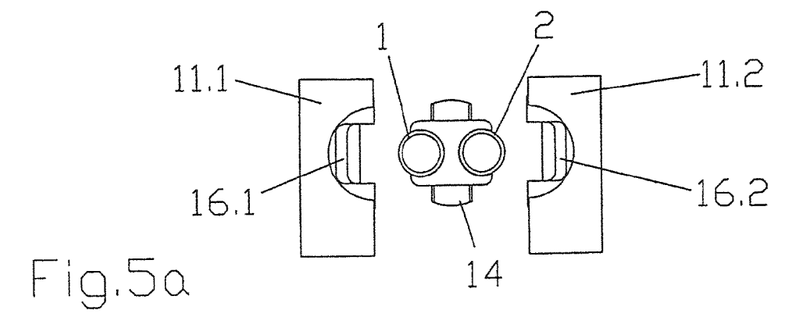
FIG. 5 shows views corresponding to FIGS. 4a-4c of the front side of the clamping jaws and of the intermediate piece with inserted hoses of the front clamping unit.
Figure 5B:
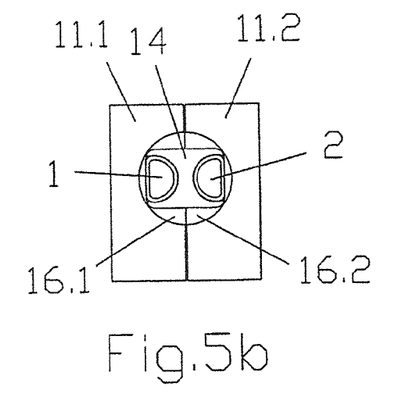
Figure 5C:
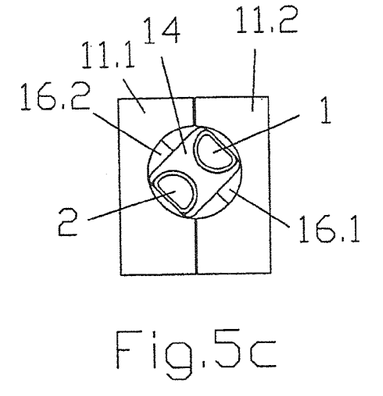

With the clamping jaws open, hoses 1 and 2 can be inserted from above into clamping units 1, 2 and be pre-secured by being pressed into the dual C-shaped profile of intermediate pieces 14, 24 at the level of their turning axis, as is evident from FIGS. 2 and 4. When moving clamping jaws 11.2 and 21.2 with the motor already mentioned into the closed setting, with intermediate pieces 14 and 24 also accompanying the motion along guides 12 or 22, the hoses, as depicted in FIG. 4b, are squeezed together in the squeezing zones until they are totally closed. Naturally, for this the longer sides of the through-passages in the squeezing zones must be dimensioned to be sufficiently long, and they assuredly can also be longer than necessary, since the hoses are centered by the dual-C-shaped profile of the intermediate pieces 14, 24 in the holding zones in the through-passages. Therefore the measure of these sides can be chosen within certain limits for differing hose diameters and does not have to be varied for adapting the apparatus to differing hose diameters.

The invention-specific apparatus can especially be used to cut through hoses 1 and 2 between the two clamping units 10 and 20, and weld their parts that arise thereby crosswise to each other, without liquid in the hoses being able to go out into the surroundings, due to the closure of the hoses achieved through squeezing together during the entire process.

So that no liquid-filled pockets can form between the squeezing zones of the two clamping units 10, 20, clamping units 10, 20 must closely adjoin, with the mutual interval being only between 3 and 5 mm, for example. In addition, for this, the two clamping units 10, 20 must be closed one after the other.

In the closed setting of both clamping units, the hoses are cut apart by the blade 3 heated to several hundred ° C. Then, with the blade still pivoted down, the capsules already mentioned are pivoted from inner clamping jaws 16.1 16.2 and intermediate piece 14 together with the hose pieces squeezed in it in clamping unit 10 by 180°. This pivoting can in turn be executed using a motor, for which the motor designated by 50 in FIGS. 1 and 2 is provided. Then blade 3 is pivoted outward and the hose ends, still hot and molten, newly brought into alignment with each other by the turning, are welded with each other by a slight motion toward each other of the two clamping units 10, 20. The guides and the drive for this motion toward each other are not depicted in the figure. Due to the small path, for this an eccentric disk can be used.

Figure 6B:
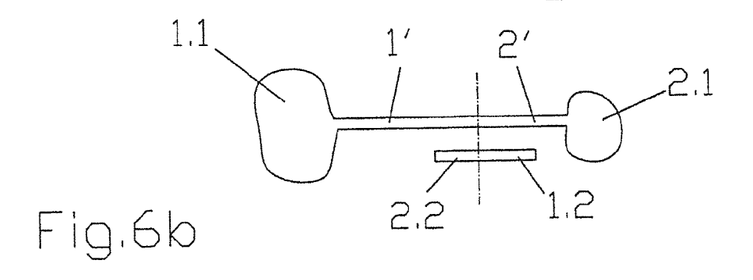
FIG. 6b is a view after connection of the hoses while using the invention-specific apparatus.

Based on an arrangement as depicted in FIG. 6a, FIG. 6b shows the result of this procedure. In FIG. 6b the two hoses 1' and 2' shorted at their end pieces are joined into a continuous hose that connects the two containers 1.1 and 2.1. On the other hand, the two end pieces are also connected with each other, and with their closed ends 1.2 and 2.2 they themselves form a closed container.

After the welding carried out as described above, clamping units 10, 20 can be moved up and hoses 1, 2 can be removed from them. Due to the mentioned rotational symmetry of inner clamping jaws 16.1 and 16.2 and of intermediate piece 14, this is possible directly, without the named pieces having to be turned additionally, such as again into their initial position. The apparatus therefore is immediately usable for welding of additional hoses.

The invention-specific apparatus can be adapted to hoses with differing diameter and/or wall thickness, merely by changing intermediate pieces 14, 24. Such hoses suited for welding typically have a diameter between ⅛ and 3 inches. As already mentioned, the measure of the longer sides of the through-passages in the squeezing zones can be selected uniformly for various hose diameters. In the holding zones it suffices to adapt the dual C-shaped profile of the intermediate pieces 14, 24 to the particular hose diameter, since the corresponding flat contact surfaces 43 on the clamping jaws are suitable for all hose diameters. For adaptation to hoses with various wall thicknesses it suffices to alter the thickness of intermediate pieces 14, 24.

Figure 7:
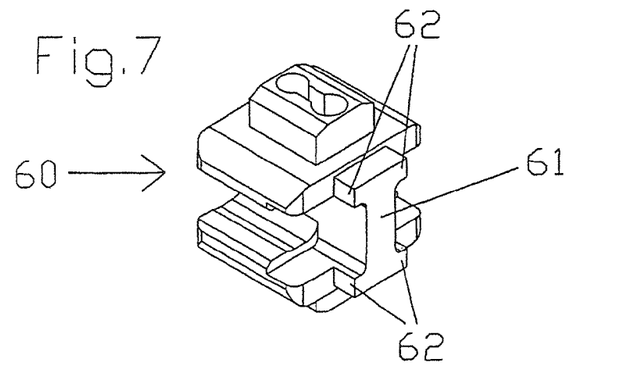
FIG. 7 is a perspective view of an intermediate piece with dual T-shaped web.
Figure 8A:
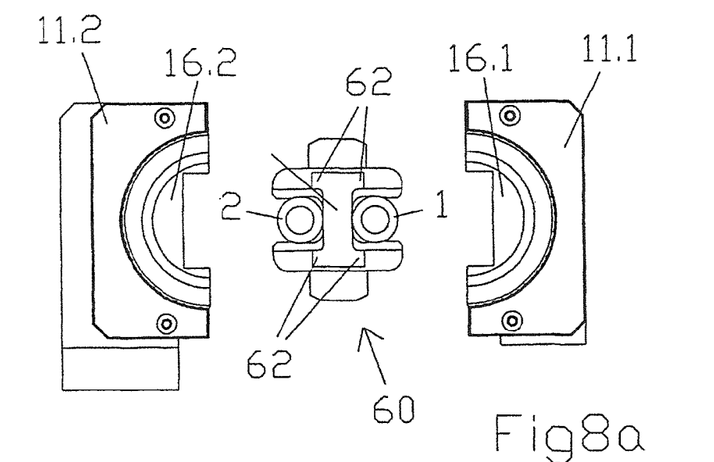
FIG. 8a is a view of the back side of the clamping jaws and of the intermediate piece from FIG. 7 with inserted hoses of the front-side clamping unit in an open state.
Figure 8B:
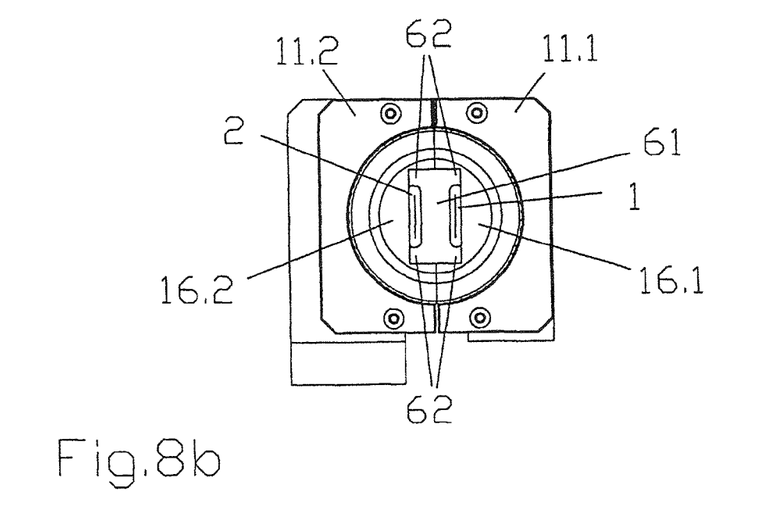
FIG. 8b is the clamping unit from FIG. 8a in a closed state.

FIG. 7 shows a version of the intermediate piece with a dual-T-shaped web. FIG. 8 shows clamping jaws 11.1, 11.2, 16.1, 16.2 of clamping unit 10 with the intermediate piece from FIG. 7 and with two inserted hoses 1, 2, with FIG. 8a showing the open position and FIG. 8b showing the closed position.

Intermediate piece 60 has a web 61, which in the closed setting of the apparatus is placed centrally between the through-passages in the area of the squeezing zones, and represents one of the longer rectangular sides of the rectangular cross section. With the dimensioning of the clamping jaws unaltered, the width of the through-passages is defined in the area of the squeezing zones by the width of web 61. This also holds true for the intermediate piece from FIG. 4.

In contrast to intermediate piece 14 from FIG. 4, web 61 of intermediate piece 60 additionally has two projections 62 on both sides, so that a dual-T-shaped profile results. These projections 62 represent the shorter rectangular sides of the rectangular cross section of the through-passages in the area of the squeezing zones and define the length of the rectangular cross sections of the through-passages in the area of the squeezing zones.

Depending on the dimensioning of web 61 and of the projections 62, and thus of the rectangular cross section of the through-passages in the area of the squeezing zone, the apparatus can be adapted by simply replacing the intermediate pieces on hoses 1, 2 with different diameters and wall thicknesses. The dimensions of the various clamping jaws do not have to be altered for that.

The width of web 61 is preferably chosen so that the width of the rectangular cross section of the through-passage in the area of the squeezing zone is 50-70% of the dual wall thickness of the hoses 1,2 to be squeezed.

This can also be done with the intermediate pieces 14 described previously. The projections 62 are preferably chosen so that the length of the rectangular cross section of the through-passage in the area of the squeezing zone is 120-140% of the diameter of the hoses 1, 2 to be squeezed.

Having described the invention, it will be apparent to those skilled in the art that alterations and modifications may be made without departing from the spirit and scope of the invention limited only by the appended claims.

The invention claimed is:

1. An apparatus for welding together at least one pair of thermoplastic hoses, said apparatus having an open position and a closed position, said apparatus comprising:
    a first clamping unit having:
        two first clamping jaws; and
        a first intermediate piece being positioned between said first clamping jaws and being configured to define first through-passages, said first through-passages being located between said respective first clamping jaws and said first intermediate piece;
        said first clamping jaws being capable of being linearly shifted relative to each other from and to the open and closed position, wherein said first through-passages are provided for inserting the at least one pair of thermoplastic hoses parallel to each other in said first through-passages in the open position, and wherein said two first clamping jaws are provided for squeezing the at least one pair of thermoplastic hoses transverse to each other in the direction of their common positional plane in the closed position, said first intermediate piece being provided for separating the at least one pair of thermoplastic hoses from each other in the closed position;
    a second clamping unit being aligned with said first clamping unit, said second clamping unit having:
        two second clamping jaws; and
        a second intermediate piece being positioned between said second clamping jaws and being configured to define second through-passages, said second through-passages being located between said respective second clamping jaws and said second intermediate piece;
        said second clamping jaws being capable of being linearly shifted relative to each other from and to the open and closed position, wherein said second through-passages are provided for inserting the at least one pair of thermoplastic hoses parallel to each other in said second through-passages in the open position, and wherein said two second clamping jaws are provided for squeezing the at least one pair of thermoplastic hoses transverse to each other in the direction of their common positional plane in the closed position, said second intermediate piece being provided for separating the at least one pair of thermoplastic hoses from each other in the closed position;
    a heatable blade for cutting through the at least one pair of thermoplastic hoses at a location between said first clamping unit and said second clamping unit and for creating at least two pairs of cut thermoplastic hoses having respective melted edges, wherein at least one pair of said cut thermoplastic hoses is located in said first clamping unit and at least one pair of said cut thermoplastic hoses is located in said second clamping, unit;
    wherein each one of said two first clamping jaws comprises an inner and an outer clamping jaw, said inner clamping jaws being respectively held by said outer clamping jaws; and
    wherein said inner clamping jaws and said first intermediate piece are capable of being turned together inside of and in relation to said outer clamping jaws during the closed position for transposing locations of said at least one pair of cut thermoplastic hoses in said first clamping unit, and for effecting the welding of said respective melted edges of said at least one pair of cut thermoplastic hoses located in said first clamping unit with said respective melted edges of said at least one pair of cut thermoplastic hoses located in said second clamping unit.

2. An apparatus according to claim 1, wherein said first through-passages include first squeezing zones and said second through-passages include second squeezing zones, each of said first squeezing zones having a first rectangular cross section and each of said second squeezing zones having a second rectangular cross section, and wherein said first rectangular cross section and said second rectangular cross section both have a length and a width, the length having longer rectangular sides and the width having shorter rectangular sides, and wherein the longer rectangular sides are oriented side-by-side parallel to each other.

3. An apparatus according to claim 2, wherein said first intermediate piece further comprises a first web being arranged centrally between said first through-passages in said first squeezing zones in the closed position, said first web being one of said longer rectangular sides of said first rectangular cross section and said second rectangular cross section.

4. An apparatus according to claim 3, wherein said first web further comprises two projections forming a dual T-shaped profile, said projections forming the shorter rectangular sides of said first rectangular cross section and said second rectangular cross section and determining a length of said first rectangular cross section and said second rectangular cross section.

5. An apparatus according to claim 2, wherein the thermoplastic hoses have a wall thickness in the unsqueezed state, wherein the width of said first rectangular cross section and said second rectangular cross section is 50-70% of two times said wall thickness.

6. An apparatus according claim 2, the thermoplastic hoses having a diameter, wherein the length of said first rectangular cross section and said second rectangular cross section is 120-140% of the diameter of the thermoplastic hoses.

7. An apparatus according to claim 2, wherein said first through-passages include first holding zones, each having a first holding zone cross section, said first holding zone cross section being wider in comparison to said first rectangular cross section of said first squeezing zones, said first holding zone cross section being wider a direction away from said first intermediate piece, and
   said second through-passages include second holding zones, each having a second holding zone cross section, said second holding zone cross section being wider in comparison to said second rectangular cross section of said second squeezing zones, said second holding zone cross section being wider a direction away from said second intermediate piece.

8. An apparatus according to claim 7, wherein said first intermediate piece and said second intermediate piece comprise dual C-shaped profiles in the holding zone for admitting and pre-securing the thermoplastic hoses.

9. An apparatus according to claim 7, wherein said inner clamping jaws have a flat contact surface for contacting the at least one pair of thermoplastic hoses in the first holding zones, and wherein said second clamping jaws have a flat contact surface for contacting the at least one pair of thermoplastic hoses in the second holding zones.

10. An apparatus according to claim 2, wherein an interval between said first squeezing zones and said second squeezing zones during cutting through the at least one pair of thermoplastic hoses is 3-6 mm.

11. An apparatus according to claim 10, wherein said interval is reduced for welding the thermoplastic hoses.

12. An apparatus according to claim 1, wherein said inner clamping jaws are secured against rotational motion in said outer clamping jaws when the first clamping jaws are in the open position.

13. An apparatus according to claim 1 further comprising a first holder for holding said first intermediate piece and a second holder for holding said second intermediate piece where the apparatus is in the open position.

14. An apparatus according to claim 1, wherein a first portion of one of said first clamping jaws and said second clamping jaws is mounted to be stationary with respect to a second portion of the other of said first clamping jaws and said second clamping jaws for insertion and removal of the at least one pair of thermoplastic hoses from said first through-passages and said second through-passages, and wherein said second portion of the other of said first clamping jaws and said second clamping jaws, said first intermediate piece and said second intermediate piece are movably mounted on linear guides.

15. An apparatus according to claim 1, wherein said inner clamping jaws and said first intermediate piece are rotationally symmetrical relative to half turns of said outer clamping jaws.

16. An apparatus for welding together thermoplastic hoses, said apparatus having an open position and a closed position, said apparatus comprising:
   a first clamping unit having two first clamping jaws with first through-passages;
   a second clamping unit having two second clamping jaws with second through-passages, said first through-passages and said second through-passages for inserting the thermoplastic hoses parallel to each other and squeezing the thermoplastic hoses transverse to each other;
   said first clamping jaws and said second clamping jaws being capable of being shifted relative to each other from and to the open position and the closed position;
   a heatable blade for cutting through the thermoplastic hoses and creating cut edges of the respective thermoplastic hoses, said heatable blade melting the respective cut edges of the thermoplastic hoses between said first clamping unit and said second clamping unit;
   a first intermediate piece being attachable between said first clamping jaws, and a second intermediate piece being attachable between said second clamping jaws, said respective intermediate pieces separating the thermoplastic hoses from each other in the closed position;
   wherein at least one of said first clamping unit and said second clamping unit further comprise inner clamping jaws and outer clamping jaws, said inner clamping jaws being held by said outer clamping jaws;
   wherein said inner clamping jaws and said respective intermediate piece are capable of being turned inside of said outer clamping jaws during the closed position;
   wherein said first through-passages include a first squeezing zone and said second through-passages include a second squeezing zone, said first squeezing zone having a first rectangular cross section and said second squeezing zone having a second rectangular cross section, and wherein said first rectangular cross section and said second rectangular cross section both comprise a length and a width, the length having longer rectangular sides and the width having shorter rectangular sides; and
   wherein said first intermediate piece further comprises a first web being arranged centrally between said first through-passages in said first squeezing zone in the closed position, said first web being one of said longer rectangular sides of said first rectangular cross section and said second rectangular cross section.

* * * * *